United States Patent
May et al.

(10) Patent No.: US 6,196,052 B1
(45) Date of Patent: Mar. 6, 2001

(54) PIEZOELECTRIC GAS SENSING DEVICE FOR DETECTION OF A GAS SPECIES A GASEOUS ENVIRONMENT

(75) Inventors: Iain May, Northwood Middlesex (GB); Glenn M. Tom, New Milford, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 09/166,674

(22) Filed: Oct. 5, 1998

Related U.S. Application Data

(63) Continuation-in-part of application No. 08/785,342, filed on Jan. 17, 1996, now Pat. No. 5,827,947.

(51) Int. Cl.[7] .......................... G01N 31/02; G01N 31/22; G01N 30/60
(52) U.S. Cl. ......................... 73/24.06; 73/31.06
(58) Field of Search ................... 73/23.31, 23.32, 73/23.35, 23.4, 24.01, 24.03, 24.04, 24.05, 24.06, 28.01, 28.04, 30.04, 31.05, 31.06, 61.45, 61.49, 61.58, 61.61, 61.75, 61.79, 64.42, 64.53; 96/143–146, 153–154; 422/50, 68.1, 83, 88, 98; 436/69, 72–84

(56) References Cited

U.S. PATENT DOCUMENTS

| | | |
|---|---|---|
| 4,111,036 * | 9/1978 | Frechette et al. ............... 73/23 |
| 4,399,686 * | 8/1983 | Kindlund et al. ............... 73/23 |
| 4,936,877 | 6/1990 | Hultquist et al. ............... 55/16 |
| 5,065,140 | 11/1991 | Neuburger ..................... 340/634 |
| 5,116,764 * | 5/1992 | Annino et al. ................. 436/161 |
| 5,151,110 * | 9/1992 | Bein et al. .................... 55/753 |
| 5,224,972 * | 7/1993 | Frye et al. .................... 55/18 |
| 5,589,396 * | 12/1996 | Frye et al. .................... 436/73 |
| 5,707,148 * | 1/1998 | Visser et al. ................... 374/31 |
| 5,731,510 * | 3/1998 | Jones et al. .................... 73/23.31 |
| 5,813,764 * | 9/1998 | Visser et al. ................... 374/12 |
| 5,814,525 * | 9/1998 | Renschler et al. .............. 436/524 |

(List continued on next page.)

OTHER PUBLICATIONS

Bright, F.V., et al, "Development of chemical sensing platforms based on sol–gel derived thin films:origin of film age vs performance trade–offs" Anal Chem., 1996, vol. 68, p. 604. (Feb. 15, 1996).

Neuburger, Glen G. "Detection of ambient hydrogen chloride with a zinc–coated piezoelectric crystal resonator operating in a frequency–time difference mode," Anal. Chem. 1989, vol. 61, pp. 1559–1563 (Jul. 15, 1989).

Levenson, Leonard L, "II. Chemisorption on single element thin films," in *Applications of piezoelectric quartz crystal microbalances*, C. Lu, editor, vol. 7, Elsevier, Amsterdam, 1984, pp. 198–203.

*Primary Examiner*—Hezron Williams
*Assistant Examiner*—Rose M. Miller
(74) *Attorney, Agent, or Firm*—Oliver A. M. Zitzmann; Steven J. Hultquist

(57) ABSTRACT

A piezoelectric gas sensing device, comprising: (a) a piezoelectric element arranged for gas sensing exposure to a gas environment; (b) a layer of a gas-retentive support material on the piezoelectric element which is retentively effective for a gas component potentially present in the gas environment; and (c) a gas-interactive material associated with the retentive support material, and sorptively effective to form a solid interaction product in interaction with the gas component potentially present in the gas environment, with the solid interaction product imparting a changed frequency response to the piezoelectric gas sensing device, in relation to a corresponding piezoelectric gas sensing device in the absence of the solid interaction product resulting from presence of the gas component in the gas environment. The device can be utilized to detect the presence and/or concentration of a gas species such as a hydride, hydrocarbon, silane, etc. in the fluid being monitored by the device.

24 Claims, 2 Drawing Sheets

U.S. PATENT DOCUMENTS

| | | | |
|---|---|---|---|
| 5,817,921 | 10/1998 | Tom et al. | 73/24.01 |
| 5,827,947 | 10/1998 | Tom et al. | 73/24.06 |
| 5,977,687 | * 11/1999 | Tom et al. | 310/316.01 |
| 6,016,689 | * 1/2000 | Bright et al. | 73/31.05 |

* cited by examiner

PIEZOELECTRIC GAS SENSING DEVICE FOR DETECTION OF A GAS SPECIES A GASEOUS ENVIRONMENT

CROSS-REFERENCE TO RELATED APPLICATION

This is a continuation-in-part of U.S. patent application Ser. No. 08/785,342 filed Jan. 17, 1996 in the names of Glenn M. Tom and Cynthia Miller, and issued Oct. 27, 1998 as U.S. Pat. No. 5,827,947, for "Piezoelectric Sensor for Hydride Gases, and Fluid Monitoring Apparatus Comprising Same.

BACKGROUND OF THE INVENTION

1. Field of the Invention

This invention generally relates to a piezoelectric gas sensing device including a piezoelectric sensing element such as a quartz crystal microbalance or a surface acoustical wave (SAW) element.

2. Description of the Related Art

In the semiconductor manufacturing industry and in other industrial process and manufacturing fields, a number of systems and techniques have been developed for monitoring a fluid, e.g., a process stream or an ambient environment in a plant facility, for the presence of specific gas components. Applications in which such fluid monitoring is carried out include monitoring of ion implant cabinets for hydride and acid gases, monitoring of process streams to determine the end point utility of a scrubber medium employed for treatment of such streams to remove hazardous gas components therefrom, and monitoring of room air for toxic gas components.

In such fluid monitoring applications, piezoelectric devices have been used for gas sensing. Examples include the use of a surface acoustical wave (SAW) element to sense concentration of a dopant species, as described in U.S. Pat. No. 4,936,877 issued Jun. 26, 1990 to Steven J. Hultquist and Glenn M. Tom for "Dopant Delivery System for Semiconductor Manufacture," and the use of quartz microbalance systems for gas stream monitoring and environmental sensor applications, as described in U.S. patent application Ser. No. 08/678,572 filed Jul. 12, 1996 in the name Glenn M. Tom and Cynthia A. Miller for "Piezoelectric End Point Sensor for Detection of Breakthrough of Fluid, and Fluid Processing Apparatus Comprising Same," U.S. patent application Ser. No. 08/679,258 filed Jul. 12, 1996 in the names of Glenn M. Tom and Cynthia A. Miller for "Piezoelectric Environmental Fluid Monitoring Assembly and Method," and U.S. patent application Ser. No. 08/785,342 filed Jan. 17, 1996 in the names of Glenn M. Tom and Cynthia A. Miller for "Piezoelectric Sensor for Hydride Gases, and Fluid Monitoring Apparatus Comprising Same," the disclosures of which hereby are incorporated herein by reference in their entireties.

In these applications, the piezoelectric element is coated with an affinity coating which is selective for particular gas species. For example, quartz crystal microbalances when used as gas sensing elements are provided with electrode coating materials that are selective for interaction with one or more gas species. Surface acoustical wave elements when employed as gas sensing elements are likewise are coated with materials selective for interaction with a desired gas species, typically as a film of the affinity coating on the top surface of the piezoelectric crystal between the respective electrode structures of the device.

In these applications, the permeability and thickness characteristics of the affinity coatings are critical to the sensitivity and speed of response of the piezoelectric device. In general, the affinity coating (which may comprise a physical adsorbent material or a chemisorbent material) should be highly available to the gas species of interest, to maximize the speed of binding or reaction of the gaseous species with the sorptive or chemically reactive sites in the affinity coating, and to maximize speed of response.

It is known to utilize porous material coatings on a quartz microbalance to provide a high surface area affinity coating, as described in the aforementioned U.S. patent application Ser. No. 08/785,342 filed Jan. 17, 1996 in the names of Glenn M. Tom and Cynthia A. Miller for "Piezoelectric Sensor for Hydride Gases, and Fluid Monitoring Apparatus Comprising Same."

The art has continued to seek improvements in piezoelectric devices for gas sensing applications.

It would be a substantial advance in the art, and is an object of the present invention, to provide an improved piezoelectric device substrate providing an enhanced interaction with the gas species of interest.

It is another object of the present invention to provide an improved surface acoustical wave device of such type.

It is a further object of the invention to provide a quartz microbalance device of such type.

Other objects and advantages of the invention will be more fully apparent from the ensuing disclosure and appended claims.

SUMMARY OF THE INVENTION

The present invention relates generally to a piezoelectric gas sensing device, comprising:

(a) a piezoelectric element arranged for gas sensing exposure to a gas environment;

(b) a layer of a gas-retentive support medium on the piezoelectric element which is retentively effective for a gas component potentially present in the gas environment; and (c) a gas-interactive material associated with (e.g., deposited on, impregnated in, etc.) the retentive support medium, and sorptively effective to form a solid interaction product in interaction with said gas component potentially present in the gas environment, said solid interaction product imparting a changed frequency response to the piezoelectric gas sensing device, in relation to a corresponding piezoelectric gas sensing device in the absence of said solid interaction product resulting from presence of said gas component in said gas environment.

In such gas sensing device the support medium may for example comprise a sol gel or polymeric material. Such a polymeric material may comprise a polymer having a glass transition temperature below the temperature of said gas sensing exposure.

As used in such context, the term "retentively effective" means that the gas-retentive support medium on the piezoelectric element takes up the gas component potentially present in the gas environment with which the gas-interactive material deposited on or otherwise associated with the retentive support medium is interactive. In other words, the gas-retentive support medium acts to retain the gas component for interaction of the gas component with the gas-interactive material, so that the overall interaction of the gas-interactive material is increased over the level of interaction that would exist in the absence of the gas-retentive support medium.

The gas-interactive material is a different material from the gas-retentive support medium. The gas-interactive material is sorptively effective—i.e., physically adsorptive and/or chemically reactive (chemisorptive) with respect to the gas component—to form a solid interaction product in interaction with such gas component when present in the gas environment. The solid interaction product imparts a changed frequency response to the piezoelectric gas sensing device, in relation to a corresponding piezoelectric gas sensing device that is devoid of the solid interaction product that otherwise results from the presence of the gas component in said gas environment.

The gas-interactive material may comprise any suitable material that generates a solid reaction product in interaction with the gas component sought to be detected in the gaseous environment, which alters the frequency response of the gas sensing device as a result of such interaction. Examples include metals, metal oxides and involatile organic and inorganic compounds. The gas-interactive material may be widely varied in the practice of the invention, depending on the gas component sought to be detected in the gaseous environment being sampled or monitored.

By use of appropriate apparatus to monitor the frequency response of the piezoelectric crystal, the presence of the gas component of interest can be detected by the change in the output frequency of the piezoelectric device or the rate of such output frequency change.

A further aspect of the invention relates to a method of detecting a gas component in a gaseous environment, by deployment of a gas sensing device of the type described hereinabove.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
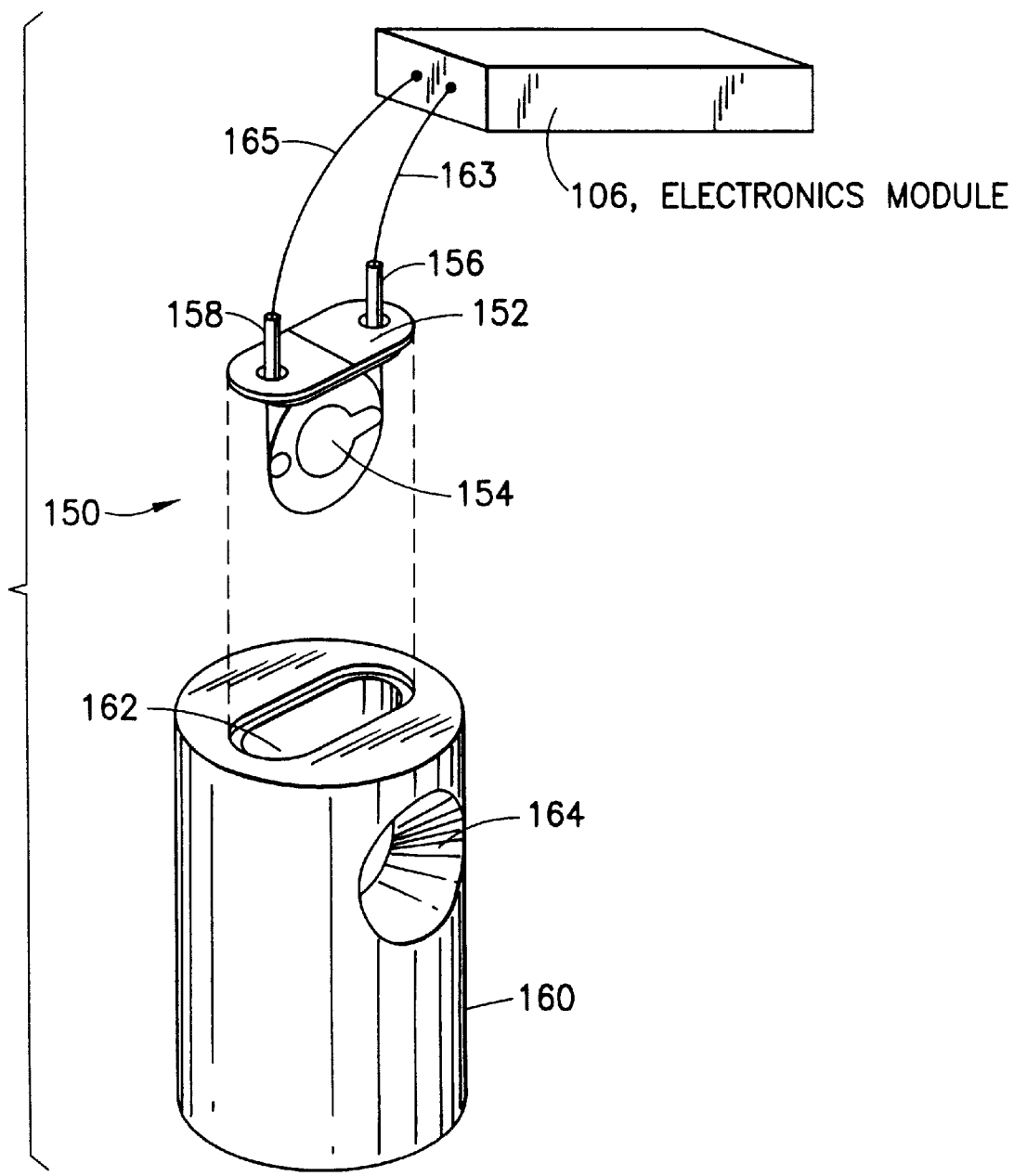
FIG. 1 is a schematic representation of a quartz crystal microbalance, such as may be used in the practice of the present invention.

The present invention relates to a piezoelectric gas sensing device for detection of one or more gas species in a gas stream potentially containing such species. The device includes a piezoelectric element arranged for gas sensing exposure to a gas environment. Such piezoelectric element may for example comprise a quartz crystal microbalance or a surface acoustical wave element.

A layer of a gas-retentive support medium is provided on the piezoelectric element. Such layer is preferably of a thin film character, having a thickness of less than about 100 microns, e.g., in the range of from about 0.001 micron to about 10 microns, more preferably from about 0.002 to about 0.2 micron, and most preferably from about 0.005 to about 0.05 micron. The gas-retentive support medium, which may be a material such as a sol gel material, polymeric material, or other matrix, resin or support medium, is retentively effective for the gas component potentially present in the gas environment that is sampled or otherwise monitored.

Such gas component is taken up by the gas-retentive support medium, e.g., by physical adsorption, solubilization, diffusional penetration, or other associative affiliation so that the gas component is present on and/or in the gas-retentive support medium. For example, the gas-retentive support medium may be a polymer that is above its glass transition temperature under the applied gas sensing conditions, so that the gas component of interest diffuses into the polymer.

A gas-interactive material, which is a different material than the gas retentive support medium, is associated with, e.g., deposited on, or impregnated in, the retentive support medium. The thickness of the gas-interactive material may likewise be of a same character as noted for the thickness of the support material hereinabove, if provided as a separate layer or film, and/or the gas-interactive material may be interspersed or otherwise integrated in the support material, so that the composite support/interactive material layer has a dimensional thickness of like character.

In general, the thickness of the gas-retentive material and the thickness of the gas-interactive material may be any suitable thickness providing the appropriate sensitivity and responsivity characteristics for the gas sensing application involved.

The gas-interactive material is sorptively (chemically and/or physically) effective to form a solid interaction product in interaction with the gas component of interest for which the gas-retentive support medium is retentively effective. The solid interaction product imparts a changed frequency response to the piezoelectric gas sensing device, in relation to a corresponding piezoelectric gas sensing device in the absence of the solid interaction product.

By this arrangement, there is a synergism between the gas-retentive support medium, which functions to provide a holding mass for the gas component of interest, so that it is localized on the support medium for interaction with the gas-interactive material. In addition, the support layer provides a base structure for the gas-interactive material, preferably providing a surface area that is increased relative to the surface of the piezoelectric element per se, so that the gas-interactive material can be utilized at a high loading on the support material, to maximize the sensitivity and operating life of the device.

In one embodiment, the support material layer may be a high surface area porous sol gel coating, which may for example be physically adsorptive for the gas component of interest, and the gas-interactive material may be a chemisorbent material that reacts with the gas component to form a solid chemical reaction product altering the frequency response character of the piezoelectric device. In such manner, the gas-interactive material reacts with the gas species of interest to produce a metal/gas interaction product of changed mass relative to the gas-interactive material initially present in the device. As a result, the mass on the piezoelectric device will change, to alter the frequency response of the piezoelectric device.

Such alteration of frequency response can be monitored and used to output an appropriate signal or alarm indicative of the presence of the gas species for which the sensor is utilized.

The support material in the piezoelectric device of the present invention may be any suitable material, such as a sol gel, a silicone oil, polyethylene glycols, methoxypolyethylene glycols, carbowax materials, polystyrenedivinylbenzene, polyvinylchloride, porous inorganic oxides (such as alumina, silica, titania, etc.), polymers in which the gas component of interest is soluble, polymers or support media that are conventionally used in supports for gas chromatography applications, etc., as well as combinations of the foregoing.

The support material may be deposited on the piezoelectric element surface by any means or methodology appropriate to the specific material constituting the support material layer. Such layer may be continuous or discontinuous in nature, and the layer may be formed by spraying, vapor deposition, chemical vapor deposition, plasma spray, dipping, roller coating, brushing, sputtering, solution deposition, etc.

The gas-interactive material may likewise be deposited on the support material in any manner appropriate to the specific material employed, including the foregoing methods illustratively identified in connection with the formation of the support material layer. The gas-interactive material may also be continuous or discontinuously applied to the support material, e.g., as a dopant, impregnant, continuous or discontinuous film on the support material, etc.

The support material may for example comprise a silica sol gel composition which is formulated and to which the gas-interactive material, e.g., a chemisorptive metal component, is added for concurrent film formation, as described hereinabove.

As another example, a silicone oil may be employed for the support material. The silicone oil is of appropriate viscosity character to provide a support matrix for the gas-interactive component, when the silicone oil material is applied to the substrate piezoelectric crystal. For example, the silicone oil may include a polysiloxane or dialkylpolysiloxane, such as dimethylpolysiloxane materials.

As another aspect of the use of such silicone formulations, the silicone component may comprise a polysiloxane or substituted polysiloxane polymer with cross-linkable functional end groups. Examples of such end groups include acrylic and methacrylic functionality which are cross-linkable in the presence of actinic radiation such as ultraviolet radiation, oxime or other functionality which is moisture curable, etc. Such cross-linkable formulations may contain appropriate promotor and initiator species to facilitate the cross-linking reaction.

As a still further embodiment, the support material may be a film-forming polyethylene glycol and/or a methoxypolyethylene glycol, e.g. of a type commercially available under the trademark Carbowax. Such glycol material may be of any suitable molecular weight characteristics, e.g., with a number average molecular weight ranging from 200 to 20,000 for polyethylene glycols and a number average molecular weight ranging from 200 to 1,000 for methoxypolyethylene glycols. Preferably, the glycol material is of a waxy or semi-solid character.

Other examples of support materials that are potentially useful in the broad practice of the invention include organic bases of sufficiently high molecular weight.

Illustrative support materials include sodium hydrogen carbonate, zinc acetate, sol gels, carbowaxes, tetrahydroxyethylenediamine and triethanolamine.

As a still further embodiment, the support material may be a composite material, and may for example comprise two or more of the above-described support materials, provided that same are compatible with one another and do not preclude the efficacy of the resulting support material for supporting the gas-interactive material.

It will be appreciated from the foregoing that the specific support material may be readily determined and employed depending on the gas-interactive material and the specific gas component to be detected by the piezoelectric device. Preferred support materials have the following characteristics:

good mass transfer characteristics (in the case of porous materials, have a high porosity or void fraction, to allow rapid movement of fluid, e.g., gas, through the support medium;

in the case of polymeric materials as the support medium, the polymer should be above its glass transition temperature at the conditions used for gas component detection, since diffusion through glassy polymers is slow and diffusion in rubbery polymers is much faster, and the gas component should have good solubility characteristics in the polymeric support medium;

good mechanical stability characteristics, preferably being stationary (in the case of polymeric support media, the polymer preferably has a viscosity of at least 2 centistokes at 210° F.); and good chemical stability (the support material preferably is not decomposible by the gas component being detected; in the case of polymers, vapor loss of the support material preferably is less than 10 picogram of material per minute at the temperature of use).

The gas-interactive material in the piezoelectric device of the invention may comprise any suitable material that is interactive with the gas species of interest to yield an interaction product that changes the frequency response of the piezoelectric device. For example, the interaction product of gas interaction with the gas-interactive material may be a chemisorption or physisorption interaction product of different mass than the initial mass of the gas-interactive material supported by the support material on the piezoelectric substrate.

The appropriate loading or concentration of the gas-interactive component for the intended end use, as may be readily determined within the skill of the art, as for example by applying to the support material on the piezoelectric substrate a series of formulations containing respectively varying concentration of the gas-interactive material therein, and evaluating the response speed, selectivity and character of the frequency response in contact of the piezoelectric device with the gas species of interest.

The interaction of the gas component with the gas-interactive material may be of any suitable type, and may for example produce reversibly bound interaction products and/or irreversible chemical reaction products.

For example, the gas-interactive material may be constituted to form films on the support medium that are useful for gas-selective irreversible reactions such as the reaction between arsine as the gas species of interest (to be sensed by the piezoelectric gas sensing device) and silver as the gas-interactive material of the device.

In applications as sensing of hydride gases, the support material preferably provides a stationary phase having negligible retention of lighter gases so that hydrides pass freely through such stationary phase to interact with the gas-interactive material supported thereby.

In one illustrative embodiment, the present invention utilizes piezoelectric crystals coated with a gas-interactive material including a metal species that is reactive with the gas species of interest, reacting to form a reaction product whose solid product component(s) on the piezoelectric crystal substrate have a different cumulative mass than the starting metal species, so that the frequency response characteristic of the piezoelectric crystal is altered in a manner that can be sensed, and preferably quantitated, to determine the presence and the concentration of the gas species.

The gas-interactive material may for example be formed as a coating comprising a metal species such as silver, chromium, copper, calcium, manganese, sodium, iron, etc., to provide highly sensitive detection of gaseous hydrides, halides and other gases, when the fluid being sensed or monitored is contacted and reacted with the reactive metal species of the gas-interactive material under operating conditions.

In the gas sensing device of the invention, the piezoelectric crystal coated with a support material/gas-interactive material coating (e.g., containing an active metal species chemically reactive with the gas component of interest) may be subjected to an input frequency, such as by an appropriately constructed and arranged oscillator circuit coupled in operative relationship to the piezoelectric crystal. The output frequency of the piezoelectric crystal coated with the support material/gas-interactive material coating then is monitored and the change of the frequency in relation to the natural harmonic frequency of the coated crystal is determined, e.g., by a cascaded counter assembly.

By this arrangement, contacting of a fluid containing the gas species of interest with the gas-reactive metal species in the coating material on the crystal will cause reaction to occur, yielding a reaction product of different mass than the initial mass of the metal component on the crystal. As a result of such mass change, the frequency response characteristics of the coated crystal will chance, and this frequency change thus will reflect the presence of the hydride or other desired gas component being monitored, in the fluid that is contacted with the coating film on the piezoelectric crystal.

The fluid component of interest that is monitored or detected by the sensor of the invention may be any suitable vapor or gas component(s) such as gases containing Group III-VII elements of the Periodic Table. An illustrative listing of gas compounds containing Group III-VII constituent elements, include, but are not limited to, gas compounds set out below.

Group III:
  Organic compounds of aluminum, gallium, and indium; hydrides of boron; gallanes, alanes, indanes and their Lewis Base complexes, e.g. trimethylamine-gallane, trimethylamine-alane.

Group IV:
  Silane, and chlorosilanes ($SiH_{4-x}Cl_x$, wherein x is an integer whose value is 1 to 4 inclusive); germane; and certain fluorinated etching agents and products; akylsilanes and alkylgermanes.

Group V:
  Hydrides of nitrogen, phosphorus, and arsenic; alkyl arsine and alkyl phosphine compounds.

Group VI:
  Hydrides of sulfur, selenium, and tellurium; alkyl selenium and alkyl tellurium compounds.

Group VII:
  Hydrogen halides (fluoride, chloride, bromide, and iodide), boron halides ($BCl_3$, $BF_3$), and chlorine ($Cl_2$).

In respect of the Group III-VII gaseous compounds, illustrative metals of the metal species potentially useful in the sensor of the invention are set out by way of example in the table below:

| Gas Compounds Containing Elements of: | Illustrative Metals of the Reactive Metal Species: |
|---|---|
| Group III | Ag, Cu, Cr, Mn, Fe |
| Group IV | Ag, Cu, Cr, Mn, Fe |
| Group V | Ag, Cu, Cr, Mn, Fe |
| Group VI | Ag, Cu, Cr, Mn, Fe |
| Group VII (HX) | MX' or MX"$_2$, ZnO | wherein X is halogen.

In the case of Group VII element-containing gases, the corresponding metal halide compounds of the table are compounds which are suitably dispersible into the support material on the piezoelectric crystal surface and which react with the Group VII compound to produce an irreversible mass change. M is a metal selected from Groups IA, IB, IIA and IIB of the Periodic Table. An example of such reaction is the metathesis reaction MX'+HX→MX+HX', wherein M=Ca, X'=I and X=Cl or F. Another example is M=Na, X'=tosylate, bicarbonate, oxide or carbonate, and X=Cl or F.

When the gas component of interest is a hydride, a metal species may constitute the gas-interactive material. Such metal species may for example comprise a metal nitrate, or a metal oxide, that is reactive with the hydride gas, e.g., arsine, phosphine, silane, germane, diborane, etc., in a redox reaction to reduce the metal compound to yield an elemental metal product, and either nitric acid or water, depending on whether the metal species is a nitrate or an oxide of the metal.

In the gas sensing device of the invention, the material coating including the support material and the gas-interactive material, must adhere to the surface of the piezoelectric crystal in a uniform manner and should not exceed the mass loading limit of a crystal that would dampen the oscillator. The response curve of the piezoelectric sensing element must be immediate, reproducible and linear.

As a particular embodiment of the present invention, a silver salt may be suspended in a sol gel matrix and employed to form an inert porous material coating on a surface of a piezoelectric crystal, thereby providing a support matrix which binds the silver salt in a manner allowing gas molecules to diffuse into the surface and react with the silver. The sol gel formulation may be carried out in a suitable manner, including mixing of silicate material such as tetraethylorthosilicate (TEOS), water, solvent, acid, and the metal salt, followed by hydrolyzing the mixture for sufficient time and temperature to permit the deposition of a suitable silica coating containing a metal salt of the desired activity.

The coating of the inert porous material containing the metal salt on the substrate may be carried out by spin-coating the sol gel metal salt solution onto the piezoelectric crystal surface. Once both sides of the crystal have been coated, the crystal must be properly stored in order to preserve the sensitivity of the sensor element (e.g., in the case of a silver nitrate-based sensor of the invention, such sensitivity preservation may involve storage of the sensor element in a dessicator in the dark, so that the silver nitrate compound in the inert porous material is protected from light and moisture).

The coating technique may be varied to achieve the desired gas sensing response, by selection and use of the amounts and proportions of TEOS, metal salt, water, solvent and acid added, the hydrolysis time and temperature, the coating technique, the gelation time, the drying time and the type of metal salt employed.

Thus, the coating formulation may be widely varied to obtain the desired quality and character of the inert porous material coating containing the reactive metal species.

The sol gel formulation utilized to form the metal species-containing coating on the piezoelectric crystal may be made using general sol gel techniques well known and established in the art, e.g., the sol gel techniques disclosed in Bright, F. V., Dunbar, R. A. and Jordan, J. D. Anal Chem. 1996, 68, 604, "Development of Chemical Sensing Platforms Based on Sol-Gel-Derived Thin Films: Origin of Film Age vs Performance Trade-Offs."

A particularly preferred reactive metal species for the piezoelectric device coating, which is responsive to the presence of arsine, phosphine and silane, as well as diborane, is silver nitrate. All four of arsine, phosphine, silane and diborane are effective reducing agents and will cause a decrease in the mass loading on the piezoelectric crystal when they react with silver nitrate.

Table One below shows the oxidation reduction reactions of arsine, phosphine, silane and diborane with silver nitrate, and the net change in molecular weight and the standard electrode potentials.

A positive e° is indicative of a favorable reaction.

The mass change of the reactive species during reaction on the piezoelectric crystal can be negative or positive, in the broad practice of the invention. The sign of the mass change will determine if the frequency increases or decreases upon exposure to the toxic gas component, or other gas impurity or trace component of interest.

TABLE ONE

Reduction Oxidation Reactions of Hydride Gases with Silver Nitrate.

| Redox Reactions | g/mol | e°(V) |
|---|---|---|
| $3AgNO_3 + AsH_3(g)\rightarrow 3Ag + As + 3HNO_3\uparrow$ | −111.5 | 1.41 |
| $3AgNO_3 + PH_3(g)\rightarrow 3Ag + 3P + 3HNO_3\uparrow$ | −155.4 | 0.91 |
| $4AgNO_3 + SiH_4(g)\rightarrow 4Ag + 4Si + 4HNO_3\uparrow$ | −219.9 | favorable |
| $6AgNO_3 + B_2H_6(g)\rightarrow 2Ag + 6B + 6HNO_3\uparrow$ | −350 | favorable |

Other metals which are reduced by arsine, silane, phosphine and diborane would also be suitable for sensing of the presence of hydride gases, as for example high valent metals such as copper, manganese, chromium, iron, etc. When sol gel techniques are used to form an inert porous material coating for a metal salt, the key parameter for the incorporation of the metal salt into the sol gel coating matrix is the solubility of the metal salt.

Cu (II) is also a viable metal species for a hydride sensor.

Set out in Table Two below is the oxidation potential for reduction of CuO with arsine and phosphine, as well as the weight changes and reactions with arsine, phosphine, silane and diborane.

TABLE TWO

Reduction Oxidation Reactions of Hydride Gases with Copper (II) Oxide.

| Redox Reactions | g/mol | e°(V) |
|---|---|---|
| $3CuO + 2AsH_3(g)\rightarrow 3Cu + 2As + 3H_2O\uparrow$ | 102.0 | 0.95 |
| $3CuO + 2PH_3(g)\rightarrow 3Cu + 2P + 3H_2O\uparrow$ | −14.0 | 0.45 |
| $2CuO + SiH_4(g)\rightarrow 2Cu + Si + 2H_2O\uparrow$ | −3.9 | favorable |
| $3CuO + B_2H_6(g)\rightarrow 3Cu + 2B + 3H_2O\uparrow$ | −26 | favorable |

Hydride gas reactions of a piezoelectric crystal coated with copper (II) nitrate- or copper (II) oxide-containing inert porous coatings, while useful to detect the presence of hydride gases, have a lower sensitivity to arsine compared to silver (I) nitrate. Such difference may be due to the smaller change in mass loading after reaction with arsine, the lower reduction potential and/or slower kinetics of the reaction. In general, higher sensitivity of the reactive gas sensing material in the inert coating is desired over lower sensitivity reactive sensor materials.

Similar sol gel techniques may be employed to prepare coatings to detect other gas types, for example acid gases. Acid gas sensors of the invention may be utilized in semiconductor manufacturing process systems in which ion implantation using boron trifluoride ($BF_3$) is employed. $BF_3$ upon exposure to air forms hydrogen fluoride (HF). Etch processes may also be employed in such semiconductor manufacturing process systems using chlorine and boron trichloride which form hydrogen chloride upon exposure to air.

In the formation of the gas sensing device as illustratively described above, the loading of a metal reactive species in an inert porous support material coating on the piezoelectric crystal may be widely varied, within the skill of the art, to provide a suitable loading with the desired frequency response characteristics for the specific end use application contemplated.

The moisture concentration in the fluid being monitored and the temperature of the fluid being monitored may affect the device response characteristics. In order to predict actual concentrations of the monitored or sensed gas component, the humidity and temperature of the gas stream or other fluid medium being monitored or sensed, is desirably measured, and the temperature of the fluid medium is appropriately controlled. The operating equation for response of the gas sensing device in hydride gas sensing service includes a concentration of gas (sensed fluid component) term, a flow rate term, and a water term, with additional noise terms for pressure and temperature. The general form of the equation is:

$$\text{Response (Hz/min/ppm/sccm)} = A[\text{Hydride}](\text{Flow Rate})(b - e^{b([H2O]-1)}) + dP/dt + d^\circ C./dt$$

where:

A=constant

[Hydride]=hydride gas (sensed fluid component) concentration in ppm flow rate=total flow of the gas stream b=constant

[H2O]=humidity in ppm

P=pressure

° C.=temperature in ° C.

t=time in minutes

In the sensor apparatus of the invention, an additional piezoelectric crystal may be employed in the sensor assembly as a reference crystal. This reference crystal desirably does not react with the gas (the sensed fluid component) but has the same fluctuations due to temperature and pressure as the sensing crystal. Such provision of an extra crystal will remove some of the noise elements in the above equation.

In the practice of the invention, particulates should be kept away from the sensor element, in order to avoid false alarms due to additional loading of the particulates on the crystal.

In some instances, wherein the gas sensing device of the invention is employed in hydride sensing service, the gas being monitored for the presence of a specific hydride may contain other hydride species, or more generally, the coating material used in the sensor may be chemically reactive with a number of species in the gas. In such instances, it may be necessary to provide ancillary pre-treatment of the gas stream or gas environment sample, to remove the species thereof which are not of interest in the monitoring or detection process.

In the broad practice of the present invention, gas-interactive material coatings with oxidizing characteristics may be utilized to detect hydride gases. For example, oxidation of a Cu, Cr, or Ag metal species to the corresponding oxide salt may be carried out for such purpose. Such oxides react with the hydrides to form non-volatile salts (and hydrogen/water). There is a net change in weight (relative to the starting sensor coating material) when such reaction occurs. Mass-sensitive piezoelectric gas sensing devices constructed in accordance with the invention can be used to readily and economically detect the occurrence of such reaction:

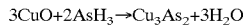

$$3CuO + 2AsH_3 \rightarrow Cu_3As_2 + 3H_2O$$

The gas sensing device of the present invention may be readily fabricated and deployed to provide accurate and reliable sensing of impurity species of interest in gas scrubbing applications. Such applications may be of the type in which a solid scavenger or chemisorbent material having removal capability for the impurity is contacted with the gas to remove the impurity therefrom, and in which the gas sensing device is utilized to determine the presence of breakthrough and/or leakage of the impurity from the bed or beds in the scrubbing system.

The gas sensing device of the present invention also has utility for environmental monitoring applications in which the coated piezoelectric crystal is provided to sense the presence of undesired components in a fluid environment such as air or other ambient gases.

FIG. 1 shows an exploded view of a gas sensing device assembly according to one embodiment of the invention, comprising a sensor element 150 and the housing 160. The sensor element 150 comprises the piezoelectric crystal 154 which is coated with a suitable material (comprising the support material and the gas-interactive material) interacting with the fluid component of interest to yield an interaction product of differing mass characteristic than the original coating material. The coated crystal is mounted on the plug member 152, with the respective leads of the piezoelectric crystal 154 protruding exteriorly of the plug member when the plug member is engaged with the housing 160 with the coated crystal extending into the cavity 162.

The housing 160 features an opening 164 by which a gas can be flowed into the cavity 162 containing the sensor element 150. Although not shown in the front perspective view of FIG. 1, the housing 160 has another opening therein, opposite opening 164 and in register with such opening, for discharge from the housing of the gas flowed past the coated piezoelectric crystal.

The leads 156 and 158 of the sensor element may be coupled in circuit relationship to suitable electronics means shown schematically as electronics module 166 in FIG. 1, by which the presence an concentration of the gas impurity species can be detected. The electronics module 166 is coupled to the sensor element leads 156 and 158 by wires 163 and 165, respectively.

Electronics module 166 provides the functions of (i) sampling the output resonant frequency of the piezoelectric crystal while the oscillating electric field is applied thereto, (ii) determining the change in resonant frequency from the fundamental resonant frequency incident to the formation of the interaction product when the sensor material interacts with the gas species in the fluid being monitored, and (iii) generating an output indicative of the presence of the gas species in such fluid.

In a specific embodiment of the sensor assembly shown in FIG. 1, the housing 160 may comprise an aluminum housing which has the cavity 162 machined into it for the insertion of the sensor element, as well as two feedthrough (¼" NPT) openings (opening 164 and the opposite opening not shown in FIG. 1) for the gas being monitored to flow through the sensor. In the body of this housing is the flow restricting orifice. Front end driver electronics are plugged directly onto the legs (leads 156 and 158) of the sensor assembly.

Figure 2:
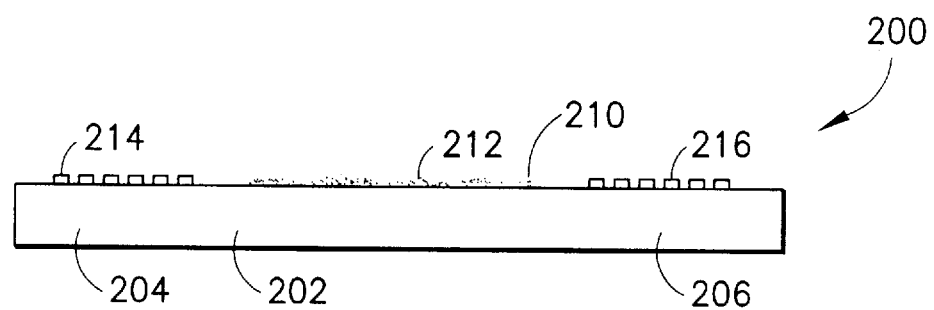
FIG. 2 is a side elevation view of a surface acoustic wave device, such as may be used in the practice of the present invention, according to one embodiment thereof.

FIG. 2 is a side elevation view of a surface acoustic wave device according to one aspect of the present invention, such as may be used for the detection or concentration monitoring of a gas species of interest.

Figure 3:
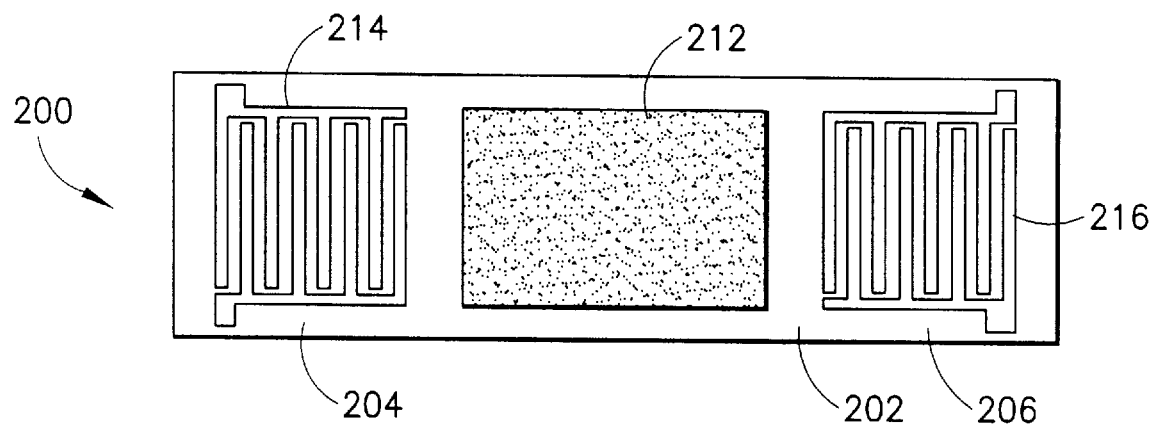
FIG. 3 is a top plan view of the surface acoustic wave device of FIG. 2.

The surface acoustic wave device 200 includes a quartz crystal 206 of thin rectangular character, as more fully shown in the top plan view of FIG. 3, wherein all parts are correspondingly numbered. The quartz crystal 202 includes a transmission end portion 204 and a reception end portion 206. End portion 204 is provided with an electrode structure 214, and receiving end portion 206 is provided with electrode structure 216 on the top surface of the crystal. Electrode structures 214 and 216 are separated by a central portion of the crystal surface having a coating 212 thereon deriving from a coating composition of the invention comprising a support material and a gas-interactive material.

The transmitting electrode structure 214 is energized to generate acoustic waves on the surface of the quartz crystal 202 that are propagated to the receiving electrode structure 216, where the acoustic wave is sensed. Fluid contacting the metal-containing film 212 and containing the gas species of interest changes the acoustic wave velocity, with the change being proportional to the number of molecules binding to the affinity coating 212 on the quartz crystal, which in turn is indicative of the presence and concentration of the gas species in the fluid with which the surface acoustic wave device is contacted.

In accordance with the invention, a multiplicity of quartz microbalance and/or surface acoustic wave sensors may be deployed, having different coatings on respective ones of such devices, to provide correction for specific gas components or conditions, by use of associated comparator circuitry and computational means, e.g., microprocessors, programmable digital computers, or the like.

The aspects and features of the present invention are more fully apparent from the following non-limiting examples, wherein all parts and percentages are by weight, unless otherwise specifically stated.

EXAMPLE I

Solution Make-up for Carbowax 20M and Silver Nitrate Quartz Crystal Microbalance Coating Solution Coating formulations were made up with the following ingredients:

| | |
|---|---|
| Acetonitrile: | Aldrich[1] part no: 27 071-7; 99.9+% |
| Silver nitrate: | Aldrich part no: 20 439-0; 99.9999% |
| Nitric acid 1.0 N in water: | Aldrich part no: 31 916-3 |
| Carbowax 20M: | Alltech[2] part no: 5069 |

[1]Aldrich Chemical Company Inc.: 1001 West Saint Paul Avenue, Milwaukee, WI 53233 USA
[2]Alltech East, 1660 Baltimore Pike, Avondale, PA 19311 USA The formulation procedure was as follows (all procedures were carried out at room temperature and pressure unless otherwise stated).

Carbowax 20M (0.268 g) was weighed and placed in a glass vial with 5 ml of acetonitrile along with a small magnetic stirring bar. The vial containing the solution was placed on a stirrer/hotplate in a light tight enclosure purged with nitrogen and maintained at 30° C. To a second vial containing a magnetic stirring bar, silver nitrate (1.698 g) was added followed by 5 ml of acetonitrile. This container was also transferred to a stirrer/hotplate within a light tight enclosure purged with nitrogen and maintained at 30° C.

Both solutions were stirred for half an hour after which period the Carbowax 20M solution was added dropwise to the acetonitrile/silver nitrate solution. This solution was capped and left stirring for a further 5 minutes. The vial containing 10 ml of acetonitrile, Carbowax 20M and silver nitrate was placed on a stirrer in a fume hood and nitric acid (1N, 3 ml) was added slowly dropwise to the acetonitrile solution. This solution was left uncapped for a further 5 minutes while stirring in a fume hood after which time it was used to spray and/or spin coat quartz crystal blanks to provide coatings having selectivity for hydride gas species such as arsine, phosphine, etc.

EXAMPLE II

Crystal Coating Method for Hydride Sensors

A coating formulation was made up with the following ingredients:

Silver nitrate 99.998%, Aldrich catalog #20 505-2 deionized water TEOS (tetraethylorthosilicate), 99.999+%, Aldrich catalog #33,385-9

Methanol anhydrous 998%, Aldrich catalog #32,241-5

Nitric acid 0.990N solution in water, Aldrich catalog #31,916-3

The formulation procedure is set out below.

Silver nitrate (1.699 g) was placed in a small vial containing a stir bar. Deionized water (0.810 g) was added and the vial was capped. The silver nitrate solution was transferred to a stir location in a temperature-controlled environment (30° C.) and was allowed to dissolve.

To another vial containing a stir bar TEOS (0.248 g) and methanol (8.942 g) were added.

Once the silver nitrate solution was completely dissolved (15 to 30 minutes) it was added dropwise into the TEOS methanol solution while the TEOS methanol solution was stirring on the stir plate. A white precipitate formed while adding the silver nitrate solution.

Upon completion of the addition of the silver nitrate solution, nitric acid (3 ml) was added which dissolved the precipitate (the solution became warm). The cap of the vial was replaced after all of the white precipitate was gone and the vial temperature had cooled.

The labeled solution was allowed to stir at a constant temperature in the dark for 18 hours and was then ready to coat quartz crystals. The viscosity of the solution was 1.50 cPoise at 22.8° C. The viscosity did not change upon examination for 44 hours. The response of the crystals after coating changed with time up until the 18-hour mark and did not change from 18 to 120 hours. The solution therefore is most suitably stirred for at least 18 hours before coating on the piezoelectric quartz crystal.

EXAMPLE III

Acid Gas Sensor

A sensor coating for acid solutions was prepared with a carbowax/NaOAc weight ratio of 1:4. This formulation was prepared to stabilize the humidity sensitivity of the gas sensing device after it was determined that coating formulations of carbowax as the support material and sodium acetate as the gas-interactive material was overly sensitive to water at low relative concentrations of carbowax (at a carbowax/sodium acetate weight ratio of 1:2, and at very high water concentrations, the coated sensors would stop oscillating). Increasing the carbowax weight fraction in the coating composition improved operability of the device markedly.

Initial work with solvent-based formulations of the carbowax, using methanol as the solvent medium, revealed carbowax to have a slow rate of dissolution. Changing of the solvent composition to replace 25% by weight of the methanol with acetonitrile, MeCN, increased the solubilization rate of the carbowax and solubilized the sodium acetate effectively. Changing the solvent composition to 100% MeCN resulted in the sodium acetate component being insoluble.

A coating formulation was therefore evolved as shown in Table Three

TABLE THREE

Materials for Acid Coating

| Material | Source | Quantity |
|---|---|---|
| Methanol | Aldrich part no: 15 490-3; 99.9+% | 75 ml |
| Acetonitrile | Aldrich part no: 27 071-7; 99.9+% | 25 ml |
| Acetic acid sodium salt trihydrate | Aldrich part no: 43 143-5 99.99%:: | 1 g ± 0.005 g |
| Carbowax 20M | Alltech part no: 5069 or Supelco | 0.5 g ± 0.005 g |

The procedure for makeup of the coating formulation is set out below.

Procedure for Solution Preparation

Weigh 0.5 g±0.02 g of carbowax 20M into a weighing funnel. Transfer the solid to a 125 ml Wheaton bottle.

Weigh 1.000 g±0.02 g of sodium acetate into a weighing funnel. Transfer the solid to the bottle.

Place a magnetic stirring bar in the bottle.

Add acetonitrile to the 25 ml mark.

Add methanol to the 100 ml mark and cap.

Place the bottle in the dark on a magnetic stirrer and stir the contents.

Once the solids are dissolved, this solution is ready for spray coating.

This solution requires no period of conditioning before or during use.

EXAMPLE IV

Hygrometer Coating

A hygrometer coating formulation was made up, for coating of a piezoelectric element, having the composition set forth in Table Four below.

TABLE FOUR

Materials for Hygrometer Coating

| Material | Source | Quantity |
|---|---|---|
| Methanol | Aldrich part no: 15 490-3; 99.9+% | 100 ml |
| Carbowax 20M | Alltech part no: 5069 or Supelco | 0.5 g ± 0.005 g |

The procedure for makeup of this formulation is set out below.

Procedure for Solution Preparation

Weigh 0.5 g±0.005 g of carbowax 20M into a Wheaton bottle, add methanol to the 100 ml mark. Place a magnetic stirring bar in the bottle and place in the dark on a magnetic stirrer This solution once mixed is ready for coating of the piezoelectric device surface. Such solution is good for one day only and requires no period of conditioning before or during use.

EXAMPLE V

Hydride Coating

A hydride coating formulation was made up, for coating of a piezoelectric element, having the composition set forth in Table Five below.

Table Five

Hydride Coating

A hydride gas detector coating formulation, for coating of a piezoelectric element surface, was made up having the composition shown in Table Five below.

TABLE FIVE

Materials for Hydride Coating

| Material | Source | Quantity |
| --- | --- | --- |
| Acetonitrile: | Aldrich part no: 27 071-7; 99.9+% | 175 ml |
| Silver nitrate: | Aldrich part no: 20 439-0: 99.9999% | 1.699 g ± 0.01 g |
| Nitric acid 1.0 N in water: | Aldrich part no: 31 916-3 | 3 ml |
| Carbowax 20M | Alltech part no: 5069 or Supelco | 0.250 g ± 0.003 g |

The procedure for makeup of the formulation is set out below.

Procedure for Solution Preparation

Weigh 0.250 g±0.003 g of carbowax 20M and 1.7 g±0.01 g of silver nitrate into a 250 ml Wheaton bottle. Add 100 ml of acetonitrile to the bottle. Place a magnetic stirring bar in the bottle. Add 3 ml of 1 N nitric acid to the mixture, bringing the total volume to 175 ml based on the mark on the Wheaton bottle.

Stir the solution in the dark until the solids are dissolved.

This solution once mixed is ready for spray coating of the piezoelectric element surface. The solution should be used within a day of its formulation.

While the invention has been described herein with reference to specific aspects, features, and embodiments, it will be apparent that other variations, modifications, and embodiments are possible, and all such variations, modifications, and embodiments therefore are to be regarded as being within the spirit and scope of the invention.

What is claimed is:

1. A piezoelectric gas sensing device, comprising:
   (a) a piezoelectric element arranged for gas sensing exposure to a gas environment;
   (b) a layer of a gas-retentive support material on the piezoelectric element which is retentively effective for a gas component potentially present in the gas environment, said layer being formed from at least one component selected from the group consisting of: tetraethylorthosilicate and methoxypolyethylene glycols, wherein the gas-retentive support material further comprises a material selected from the group consisting of silicone oils, polyethylene glycols, sodium hydrogen carbonate, zinc acetate, tetrahydroxyethylenediamine and triethanolamine; and
   (c) a gas-interactive material associated with the gas-retentive support material, and sorptively effective to form a solid interaction product in interaction with said gas component potentially present in the gas environment, said solid interaction product imparting a changed frequency response to the piezoelectric gas sensing device, in relation to a corresponding piezoelectric gas sensing device in the absence of said solid interaction product, resulting from presence of said gas component in said gas environment, wherein the gas interactive material comprises at least one component selected from the group consisting of: silver and acetate species.

2. The gas sensing device according to claim 1, wherein the gas-retentive support material is porous.

3. The gas sensing device according to claim 1, wherein the gas-interactive material is deposited on the retentive support material.

4. The gas sensing device according to claim 1, wherein the gas-interactive material is dispersed in the retentive support material.

5. The gas sensing device according to claim 1, wherein the gas-retentive support material comprises a porous polymer.

6. The gas sensing device according to claim 1, further comprising a base receptor material.

7. The gas sensing device according to claim 1, wherein the gas-interactive material further comprises a metal selected from the group consisting of copper, zinc, calcium, manganese, sodium, iron, chromium, and combinations of two or more of the foregoing.

8. The gas sensing device according to claim 1, wherein the gas-interactive material further comprises a metal nitrate.

9. The gas sensing device according to claim 1, wherein the piezoelectric element comprises a surface acoustic wave piezoelectric element.

10. The gas sensing device according to claim 1, wherein the piezoelectric element comprises a quartz crystal microbalance piezoelectric element.

11. A method of detecting a gas component in a gas environment, comprising:
   (I) providing a piezoelectric gas sensing device, comprising:
      (a) a piezoelectric element arranged for gas sensing exposure to a gas environment;
      (b) a layer of a gas-retentive support material on the piezoelectric element which is retentively effective for the gas component potentially present in the gas environment, said layer comprising at least one component selected from the group consisting of: tetraethylorthosilicate and methoxypolyethylene glycols, wherein the gas-retentive support material further comprises a material selected from the group consisting of silicone oils, polyethylene glycols, sodium hydrogen carbonate, zinc acetate, tetrahydroxyethylenediamine and triethanolamine; and
      (c) a gas-interactive material associated with the retentive support material, and sorptively effective to form a solid interaction product in interaction with said gas component potentially present in the gas environment, said solid interaction product imparting a changed frequency response to the piezoelectric gas sensing device, in relation to a corresponding piezoelectric gas sensing device in the absence of said solid interaction product resulting from presence of said gas component in said gas environment, wherein the gas interactive material comprises at least one component selected from the group consisting of: silver ions and acetate; and (II) exposing the piezoelectric device to the gas environment to cause the gas component present in the gas environment to be retained by the support medium and to interact with the gas-interactive material to alter the frequency response of the piezoelectric device; and (III) outputting an output correlative of the frequency response alteration and indicative of the presence of the gas component in the gas environment.

12. The gas method according to claim 11, wherein the gas-retentive support material is porous.

13. The method according to claim 11, wherein the gas-interactive material is deposited on the retentive support material.

14. The method according to claim 11, wherein the gas-interactive material is dispersed in the retentive support material.

15. The method according to claim 11, wherein the gas-retentive support material further comprises a material selected from the group consisting of sol gel materials, gas chromatography stationary phase materials, and organic bases.

16. The method according to claim 11, wherein the support material comprises a porous polymer.

17. The method according to claim 11, wherein the gas-sensing device further comprises a base receptor material.

18. The method according to claim 11, wherein the gas-interactive material further comprises a metal selected from the group consisting of copper, zinc, calcium, manganese, sodium, iron, chromium, and combinations of two or more of the foregoing.

19. The method according to claim 11, wherein the gas-interactive material further comprises a metal nitrate.

20. The method according to claim 11, wherein the piezoelectric element comprises a surface acoustic wave piezoelectric element.

21. The method according to claim 11, wherein the piezoelectric element comprises a quartz crystal microbalance piezoelectric element.

22. A piezoelectric gas sensing device, comprising:

(a) a piezoelectric element arranged for gas sensing exposure to a gas environment;

(b) a layer of a gas-retentive support material on the piezoelectric element which is retentively effective for a gas component potentially present in the gas environment, said layer being formed from at least one component selected from the group consisting of: tetraethylorthosilicate and methoxypolyethylene glycols; and (c) a gas-interactive material associated with the gas-retentive support material, and sorptively effective to form a solid interaction product in interaction with said gas component potentially present in the gas environment, said solid interaction product imparting a changed frequency response to the piezoelectric gas sensing device, in relation to a corresponding piezoelectric gas sensing device in the absence of said solid interaction product, resulting from presence of said gas component in said gas environment, wherein the gas interactive material comprises at least one component selected from the group consisting of: silver and acetate species;

wherein the gas-retentive support material and gas-interactive material are formed together by applying to the piezoelectric element a coating solution selected from the group consisting of: (i) a coating solution comprising methoxypolyethylene glycol and silver nitrate; and (ii) a coating solution comprising tetraethylorthosilicate and silver nitrate.

23. The device of claim 22 wherein the gas-retentive support material and gas-interactive material are formed together by applying to the piezoelectric element a coating solution comprising acetic acid and methoxypolyethylene glycol.

24. The device of claim 22 wherein the gas-retentive support material and gas-interactive material are formed together by applying to the piezoelectric element a coating solution comprising methoxypolyethylene glycol and silver nitrate.

* * * * *